United States Patent [19]
Zuck

[11] Patent Number: 6,050,988
[45] Date of Patent: Apr. 18, 2000

[54] DEVICE FOR ENHANCING TRANSDERMAL AGENT FLUX

[75] Inventor: Michael G. Zuck, Bend, Oreg.

[73] Assignee: ALZA Corporation, Mountain View, Calif.

[21] Appl. No.: 09/208,312

[22] Filed: Dec. 9, 1998

Related U.S. Application Data

[60] Provisional application No. 60/069,340, Dec. 11, 1997.

[51] Int. Cl.⁷ .............................. A61K 9/22; A61N 1/30; A61B 17/20
[52] U.S. Cl. ........................... 604/890.1; 604/22; 604/20; 600/362
[58] Field of Search .......................... 604/20–22, 46–47, 604/890.1; 128/114.1, 907; 600/306, 362, 556; 424/9.8, 9.81, 449

[56] References Cited

U.S. PATENT DOCUMENTS

| | | | |
|---|---|---|---|
| Re. 25,637 | 9/1964 | Kravitz et al. | 128/253 |
| 3,072,122 | 1/1959 | Rosenthal | 128/253 |
| 3,322,121 | 5/1967 | Banker | 128/253 |
| 3,814,097 | 6/1974 | Ganderston et al. | 128/268 |
| 3,905,371 | 9/1975 | Stickl et al. | 128/253 |
| 3,918,449 | 11/1975 | Pistor | 128/218 |
| 3,964,482 | 6/1976 | Gerstel et al. | 128/260 |
| 4,340,048 | 7/1982 | Eckenhoff | 128/213 |
| 4,379,454 | 4/1983 | Campbell et al. | 604/897 |
| 4,588,580 | 5/1986 | Gale et al. | 424/21 |
| 4,655,766 | 4/1987 | Theeuwes et al. | 604/896 |
| 4,698,062 | 10/1987 | Gale et al. | 604/896 |
| 4,753,651 | 6/1988 | Eckenhoff | 424/449 |
| 4,756,314 | 7/1988 | Eckenhoff et al. | 128/760 |
| 4,832,953 | 5/1989 | Campbell et al. | 424/448 |
| 4,867,982 | 9/1989 | Campbell et al. | 424/449 |
| 5,080,646 | 1/1992 | Theeuwes et al. | 604/20 |
| 5,108,819 | 4/1992 | Heller et al. | 428/195 |
| 5,147,296 | 9/1992 | Theeuwes et al. | 604/20 |
| 5,169,382 | 12/1992 | Theeuwes et al. | 604/20 |
| 5,169,383 | 12/1992 | Gyory et al. | 604/20 |
| 5,242,406 | 9/1993 | Gross et al. | 604/132 |
| 5,250,023 | 10/1993 | Lee et al. | 604/20 |
| 5,268,209 | 12/1993 | Hunt et al. | 428/34.3 |
| 5,279,543 | 1/1994 | Glickfeld et al. | 604/20 |
| 5,279,544 | 1/1994 | Gross et al. | 604/20 |
| 5,310,404 | 5/1994 | Gyory et al. | 604/20 |
| 5,312,456 | 5/1994 | Reed et al. | 411/456 |
| 5,362,307 | 11/1994 | Guy et al. | 604/20 |
| 5,385,543 | 1/1995 | Haak et al. | 604/20 |
| 5,391,250 | 2/1995 | Cheney, II et al. | 156/268 |
| 5,423,739 | 6/1995 | Phipps et al. | 604/20 |
| 5,438,984 | 8/1995 | Schoendorfer | 128/632 |
| 5,569,272 | 10/1996 | Reed et al. | 606/161 |
| 5,611,806 | 3/1997 | Jang | 606/167 |
| 5,879,326 | 3/1999 | Godshall et al. | 604/51 |
| 5,964,729 | 10/1999 | Choi et al. | 604/47 |

FOREIGN PATENT DOCUMENTS

| | | | |
|---|---|---|---|
| 0 497 620 A2 | 8/1992 | European Pat. Off. | F16B 5/07 |
| 195 18 974 | 11/1995 | Germany | A61M 37/00 |
| 195 18 974 A1 | 11/1995 | Germany | A61M 37/00 |
| WO 96/17648 | 6/1996 | WIPO | A61N 1/30 |
| WO 96/37155 | 11/1996 | WIPO | A61B 17/20 |
| WO 96/37256 | 11/1996 | WIPO | A61N 1/30 |
| WO 97/07734 | 3/1997 | WIPO | A61B 5/00 |

OTHER PUBLICATIONS

Reiss, Susan M., Biophotonics International, May/Jun. 1997, pp 43–45, "Glucose– and Blood–Monitoring Monitoring Systems vie for Top Spot".

Eppstein, Jonathan, et al. presented Dec. 15–18, 1997 at transdermal delivery conference sponsored by IBC in San Diego, "Rapid Transdermal Drug Delivery with Thermal Micro–Poration".

*Primary Examiner*—Sharon Finkel
*Attorney, Agent, or Firm*—D. Byron Miller; Steven F. Stone

[57] ABSTRACT

A device (2) comprising a sheet member (6) having a plurality of microprotrusions (4) extending from a bottom edge (5) for penetrating the skin of a patient. The sheet member (6) when in use being oriented in an approximately perpendicular relation to the patient's skin.

26 Claims, 7 Drawing Sheets

DEVICE FOR ENHANCING TRANSDERMAL AGENT FLUX

This application claim the benefits of provisional application U.S. Ser. No. 60/069,340 filed Dec. 11, 1997 under 35 U.S.C. §119(e).

TECHNICAL FIELD

The present invention relates to transdermal agent delivery and sampling. More particularly, this invention relates to the transdermal delivery of agents, such as peptides and proteins, through the skin, as well as the transdermal sampling of agents from the body, such as glucose, other body analytes and substances of abuse, such as alcohol and illicit drugs.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to their large size/high molecular weight and the resulting inability to pass through natural pathways (pores, hair follicles, etc.) through skin. In addition, polypeptides and proteins are easily degradable during penetration of the skin, prior to reaching target cells. Likewise, the passive flux of water soluble small molecules such as salts is limited.

One method of increasing the transdermal delivery of agents relies on the application of an electric current across the body surface or on "electrotransport". "Electrotransport" refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported. Electrotransport delivery generally increases transdermal flux of agents, particularly large molecular weight species (e.g., polypeptides), relative to passive or non-electrically assisted transdermal delivery. However, further increases in transdermal delivery rates and reductions in polypeptide degradation during transdermal delivery are highly desirable.

One method of increasing the agent transdermal delivery rate involves pre-treating the skin with, or co-delivering with the beneficial agent, a skin permeation enhancer. The term "permeation enhancer" is broadly used herein to describe a substance which, when applied to a body surface through which the agent is delivered, enhances its flux therethrough. The mechanism may involve a reduction of the electrical resistance of the body surface to the passage of the agent therethrough, an increase in the permselectivity and/or permeability of the body surface, the creation of hydrophilic pathways through the body surface, and/or a reduction in the degradation of the agent (e.g., degradation by skin enzymes) during electrotransport.

There have been many attempts to mechanically disrupt the skin in order to enhance transdermal flux, such as, U.S. Pat. Nos. 3,814,097 issued to Ganderton et al., 5,279,544 issued to Gross et al., 5,250,023 issued to Lee et al., and 3,964,482 issued to Gerstel et al., U.S. Pat. No. Re. 25,637 issued to Kravitz et al. and published PCT applications WO 96/37155; WO 97/48440; and WO 97/48441. These devices typically utilize tubular or cylindrical structures generally, although the Gerstel U.S. Patent and the latter two PCT publications do disclose the use of other shapes, to pierce the outer layer of the skin. The piercing elements disclosed in these references generally extend perpendicular from a thin flat member, such as a pad or metal sheet, which is placed on the skin surface. The flexible nature of the flat member and the tubular shape of the piercing elements result in a variety of short-comings, such as manufacturing difficulties, flexing of the flat member when pressure is applied to the top of the device, uneven or poor penetration of the skin by the microblades or microtubes resulting in low transdermal agent flux and, for electrotransport, increased irritation due to concentrating the drug flux through fewer pathways.

A further shortcoming of the devices disclosed in WO 97/48440 and WO 97/48441 concerns the degree of difficult in their manufacture. First, the thin flexible metallic sheets/plates must be subjected to a photoetching process to form openings in the sheet/plate through which the agent being transdermally delivered or sampled can pass. The photo-etching is also used to form the microblades. However, a second punching step is required to bend the microblades to an angle roughly perpendicular to the plane of the sheet. Because of the tiny size of the openings (about 0.4=0.5 mm) and because of the large number of openings (about 50 to 300 openings/cm$^2$), accurate alignment of the micropunches with the microopenings is problematic and time consuming.

DESCRIPTION OF THE INVENTION

The present invention provides a device suitable for increasing transdermal agent flux. The device has microprotrusions which consistently and reliably penetrate a body surface (e.g., skin) to enhance agent delivery or sampling. The device of the present invention can be manufactured in high volumes and at low-cost. The device of the present invention can penetrate the stratum corneum of skin with a plurality of microprotrusions to form pathways through which a substance such as a drug can be introduced (i.e., delivery) or a substance such as a body analyte can be withdrawn (i.e., sampling). A principal advantage of the present invention is that the device ensures uniform penetration (i.e., generating the same size and depth pathways) by the microprotrusions across the width of the device. Furthermore, the present invention reproducibly provides uniformity in penetration from patient to patient.

In one aspect, the invention comprises a rigid structure which comprises a thin sheet which in use is oriented with its width perpendicular to the patient's body surface. The sheet has a plurality of microprotrusions in the same plane as the sheet and extending outward from a body proximal edge of the sheet for piercing the body surface. The thin sheet transmits force applied to a body distal edge of the sheet to the microprotrusions with substantially less dissipation of the application force in the thin sheet than prior art devices. The rigid structure formed by the thin sheet provides assured transmittance of an externally applied load to the microprotrusions without wasting energy in deflection of any portion of the device for easier, complete and reproducible skin penetration. The improved penetration of the skin by the microprotrusions because of the rigid structure formed by the thin sheet is particularly beneficial in producing increased agent flux. The transmitted load provides nearly complete penetration by all of the microprotrusions so as to produce a substantial number of microslits in the stratum corneum for continued and reproducible transdermal agent flux. Optionally, though preferably, the rigid structure forms a void for containing an agent reservoir. The void can be filled with a reservoir material for containing the agent to be delivered or sampled.

The sheet with the plurality of microprotrusions can be manufactured more easily and less expensively than the prior art designs comprised of a thin sheet having blades punched perpendicularly therefrom since the present invention does not require a separate punching operation.

In one aspect of the invention, the device utilizes a plurality of spaced sheet members which are fastened together in a roughly parallel configuration, each of the sheet members having a plurality of croprotrusions extending downward from their body proximal edges.

In another aspect of the invention, the device utilizes a sheet member folded in a serpentine configuration and having a plurality of microprotrusions extending downward from the body proximal edge of the sheet member.

In another aspect of the invention, the device utilizes a plurality of cylindrical sheet members forming concentric circles having a plurality of microprotrusions extending downward from their body proximal edges, respectively.

In yet another aspect of the invention, the device utilizes a sheet member coiled in a loose spiral and having a plurality of microprotrusions extending downward from the body proximal edge of the sheet member.

Optionally, though preferably, the device has a rigid support member contacting the body distal edge(s) of the sheet member(s) opposite the body proximal edge. The device of the present invention can be used in connection with agent delivery, agent sampling or both. In particular the device of the present invention is used in connection with transdermal drug delivery, transdermal analyte sampling, or both. Delivery devices for use with the present invention include, but are not limited to, electrotransport devices, passive devices, osmotic devices and pressure driven devices. Sampling devices for use with the present invention include, but are not limited to, reverse electrotransport devices, passive devices, negative pressure driven, and osmotic devices.

BRIEF DESCRIPTION OF THE DRAWINGS

In the figures, like reference numerals refer to like elements in the several drawings.

MODES FOR CARRYING OUT THE INVENTION

Figure 1:
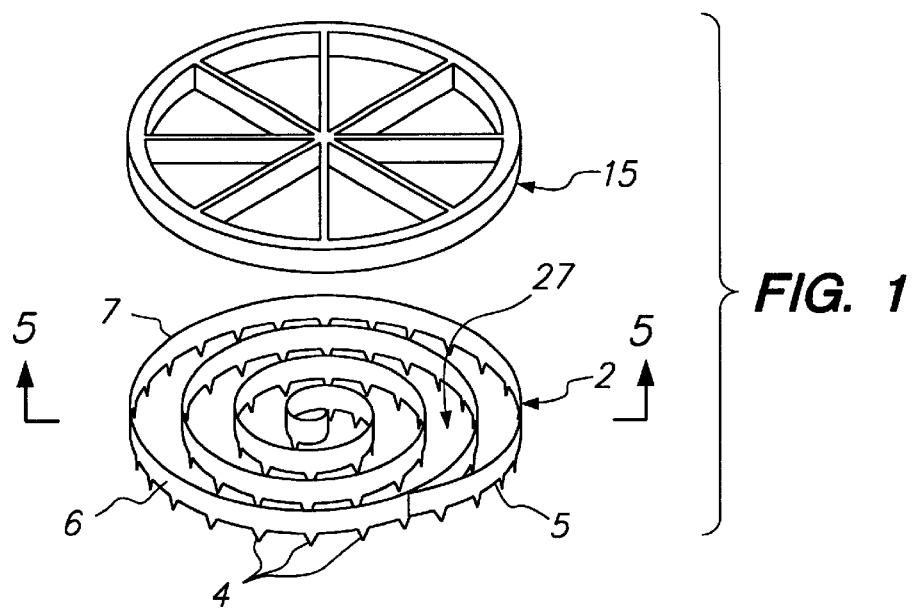
FIG. 1 is a perspective view of a first embodiment of a skin penetrating sheet member and a rigid support therefor.

Turning now to the drawings in detail, the skin penetrating and reservoir device 2 of the present invention is generally shown in FIG. 1 for use in the percutaneous administration or sampling of an agent. The terms "substance", "agent" and "drug" are used interchangeably herein and broadly include physiologically or pharmacologically active substances for producing a localized or systemic effect or effects in mammals including humans and primates, avians, valuable domestic household, sport or farm animals, or for administering to laboratory animals such as mice, rats, guinea pigs, and the like. These terms also include substances such as glucose, other body analytes found in the tissue, interstitial fluid and/or blood, substances such as alcohol, licit substances, illicit drugs, etc. that can be sampled through the skin. The major barrier properties of the skin, such as resistance to agent electrotransport of water soluble drugs, reside with the outer layer (i.e., stratum corneum). The inner portions of the epidermis generally comprise three layers commonly identified as stratum granulosum, stratum malpighii, and stratum germinativum. There is much lower resistance to transport or to absorption of an agent through the stratum granulosum, stratum malpighii, and stratum germinativum compared to the resistance to agent transport through the stratum corneum. Thus, the microprotrusions 4 penetrate at least through the stratum corneum so that the agent is conducted with little or no resistance through the skin.

Figure 2:
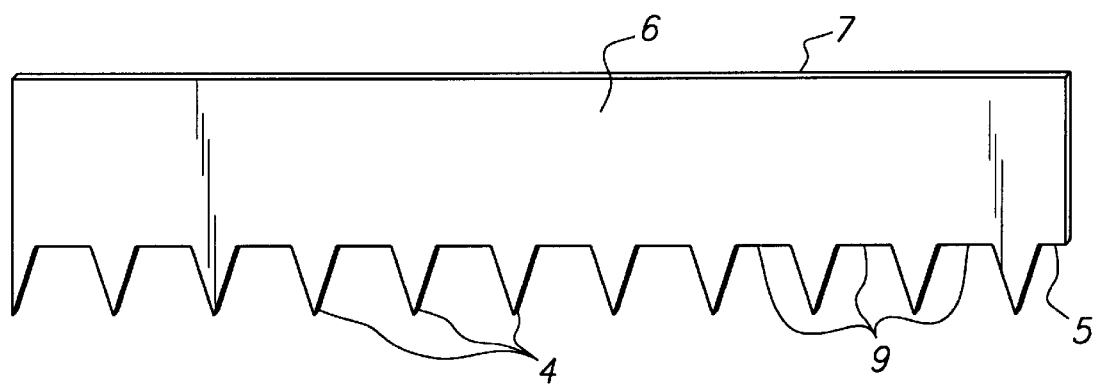
FIG. 2 is a front elevational view of a portion of the sheet member of FIG. 1 prior to being coiled.
Figure 3:
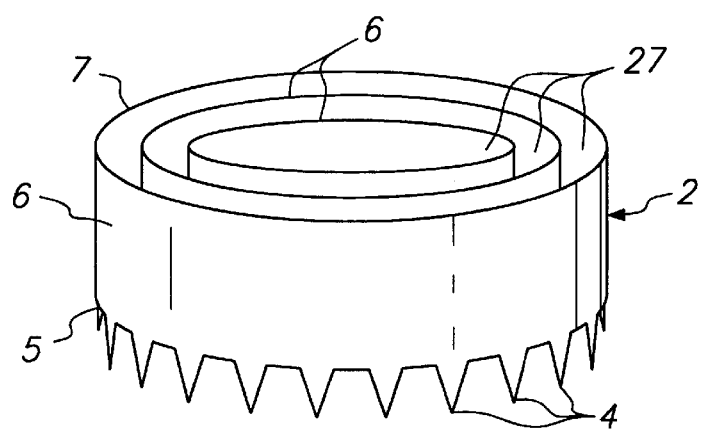
FIG. 3 is a perspective view of a second embodiment of a skin penetrating sheet member.
Figure 4:
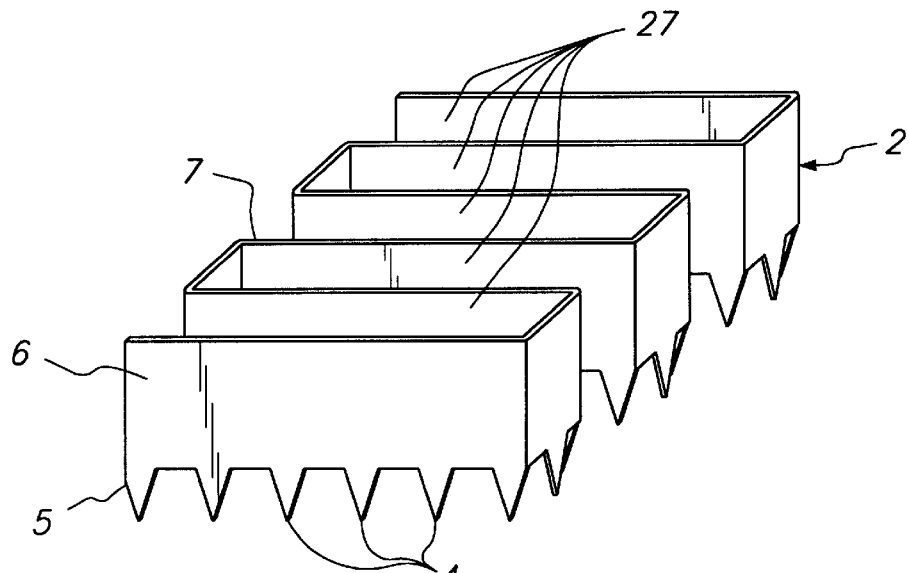
FIG. 4 is a perspective view of a third embodiment of the skin penetrating sheet member.

Device 2 comprises a plurality of microprotrusions 4 extending outward from edge 5 (also referred to as the body proximal edge) of a thin, sheet member or strip 6 (FIG. 2). Sheet member 6 is generally compliant and flexible because of its relatively thin thickness, for example, about 5 μm to about 100 μm, preferably about 25 μm to about 50 μm. Coiling (FIG. 1), folding (FIGS. 4 and 7), curving (FIG. 3), stacking (FIG. 15), as well as other forms of forming the sheet member 6 from its generally planer state along its entire length, form a rigid structure having a plurality of voids 27, 127 for holding a reservoir that contains the agent that is to be delivered or that is adapted to receive the agent that is to be sampled. Those skilled in the art will appreciate that spacers can be placed within voids 27, optionally secured together with fasteners such as fastening bolts or pins, to keep the spacing between adjacent turns (FIG. 1) or folds (FIG. 4) of sheet member 6 constant. To prevent deformation or flexing side to side of sheet member 6 as the microprotrusion array is applied to the body surface, support member 15 is preferably placed across the skin distal edge 7 (also referred to as the top edge) of sheet member 6 (FIGS. 1 and 5).

Figure 5:
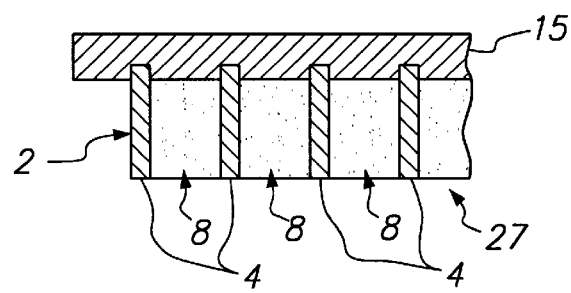
FIG. 5 is a cross-sectional view of the rigid support and skin penetrating sheet member of FIG. 1 taken along line 5—5 with an agent-containing material within the voids between successive spirals of the sheet member.

Optional support member 15 can be a variety of configurations, for example but not limited to the embodiments shown in FIGS. 1 and 5. The support member 15 transmits force that is applied to the top of the support member across the skin distal edge 7 of sheet member 6 so that each of the microprotrusions 4 receive substantially the same amount of force for penetrating the skin. Force applied to the edge 7, and directed toward the skin, causes the microprotrusions 4 to pierce at least through the stratum corneum.

Various embodiments of the device 2 are illustrated in the figures although other configurations beyond those specifically illustrated are within the scope of the invention. In each of these embodiments, the device 2 is comprised of sheet member 6, or a plurality of sheet members 6, 106 (see FIGS. 3 and 15) having their width oriented generally perpendicular to a body surface (e.g., skin), thereby forming vertical walls, to efficiently (i.e., without bending or flexing the sheet member 6) transmit a force applied across the skin distal edge 7 of the sheet member 6 to the microprotrusions 4. The width (i.e., the distance from the skin distal edge to the skin proximal edge) of the sheet member 6 is optionally, though preferably, sufficient to create a plurality of voids 27 for the agent reservoir. The number and the volume of voids 27 depends on a variety of factors, for example, the relative structural integrity or flexibility of the sheet member 6, the distance across the device 2, the size of the agent reservoir skin-contact area, and the reservoir volume required for the therapy (in the case of drug delivery from the reservoir).

Figure 15:
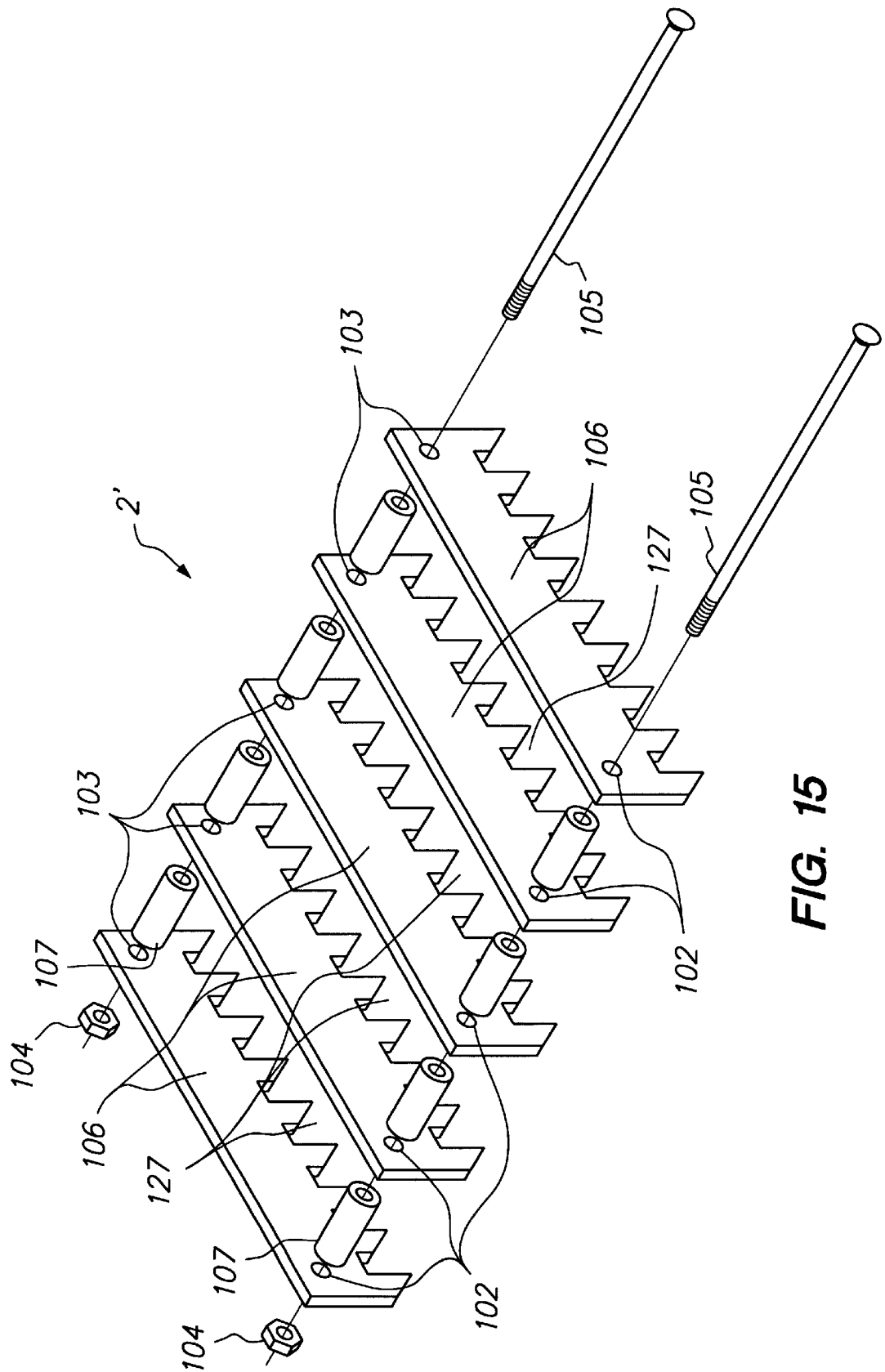
FIG. 15 is an exploded view of another embodiment of the skin penetrating sheet member.

A particularly preferred configuration for the device is illustrated in FIG. 15 and comprises a plurality of individual sheet members 106 stacked together to form device 2'. Each of the sheet members 106 has a pair of holes 102, 103, through which bolts 105 are inserted. Spacers (e.g., tubes) 107 are positioned between each adjacent pair of sheet members 106 to form voids 127 therebetween. The spaced sheet members 106 are held together as a unit by securing nuts 104 on the ends of bolts 105, or using other known fasteners. As in the FIG. 1 device, the voids 127 can be filled with a reservoir matrix material (e.g., a gel) adapted to contain the beneficial agent to be delivered or to receive the body analyte to be sampled. Those skilled in the art will appreciate that spacers having other than tube-like configurations (e.g., square or rectangular blocks) can also be used to provide voids 127 between adjacent sheet members 106 as long as the spacers do not form a complete barrier between the agent reservoir 8 (i.e., the agent reservoir contained in the voids 127) and the skin. Furthermore, more than two sets of bolts 105, or other fastening pins, may be used to secure the sheet members 106 and spacers 105 together.

The microprotrusions 4 can be microblades or any of a variety of configurations for piercing the skin or body surface. The microprotrusions 4 penetrate the stratum corneum of the epidermis when pressure is applied to the top (body distal side) of the support member 15 to increase the administration of, or sampling of, an agent through a body surface. The term "body surface" as used herein refers generally to the skin, mucous membranes, and nails of an animal or human, and to the outer surface of a plant. The microprotrusions 4 penetrate the body surface to create good agent conduction from the system into the body, or vice versa. In some configurations, spaces 9 (see FIG. 2) are formed between each of the microprotrusions 4 to create a lower blade density and/or to provide "stops" which prevent the device from penetrating the body surface beyond the length of the microprotrusions 4. The agent can be administered or sampled at a controlled rate of release from or collection in the voids 27 housing the agent-containing or agent-receiving reservoir through an agent rate controlling material such as a flux control membrane (not shown) positioned between the voids 27, 127 and the body surface.

The microprotrusions or microblades 4 are generally formed from a single piece of material (as shown in FIG. 2) and are sufficiently sharp and long for penetrating at least the stratum corneum of the skin. In one embodiment, the microprotrusions 4 and the sheet member 6 are essentially impermeable or are impermeable to the passage of an agent. The width of each microprotrusion 4 can be any of a range of widths. The width of the microprotrusion 4 at the intersection of the microprotrusion and the body surface after the microprotrusion array has been inserted is typically at least about 25 μm. The required length of the blades is subject to variation of the body surface being penetrated and corresponds to at least the natural thickness of the stratum corneum, for one of the principal features of the invention is that the microprotrusions are to penetrate at least through the stratum corneum and into the epidermis. Usually, the microprotrusions 4 will have a length and configuration which achieves a depth of penetration of about 25 μm to about 400 μm, with the depth of penetration for most applications being between about 50 μm to about 200 μm. The microprotrusions 4 can have slanted (i.e., angled) leading edges to further reduce the insertion force required to press the microprotrusions into the skin tissue. The leading edges of each microprotrusion 4 can all be the same angle or can be at different angles suitable for penetrating the skin. Alternatively, the leading edge of each microprotrusion 4 can be curved having, for example, a convex or concave shape or be divided into any number of angled segments such as the first segment being relatively steep with respect to vertical and the second segment being more gradually angled with respect to vertical.

The sheet member 6 of the present invention can optionally include microprotrusion anchoring means for improving the attachment of the device to the skin so that a continuous agent conducting pathway through the body surface is preserved even during movement of the patient and/or the patient's body surface. Some or all of the microprotrusions 4 can have a barb which assists in anchoring the sheet member 6 and any corresponding device or structure used in combination therewith to the skin. Microblade anchoring barbs are described in more detail in WO 97/48440, and Reed et al. U.S. Pat. Nos. 5,312,456 and 5,569,272 of which any of the disclosed configurations can be used with the present invention. The barbs are but one example of microprotrusion anchoring means. In addition to anchoring means on the blades, other means for holding the device in contact with the skin can be used, such as but not limited to adhesive agent-containing reservoirs in the voids 27, 127, peripheral adhesive, tape, a strap, or an elastic bandage.

Figure 6:
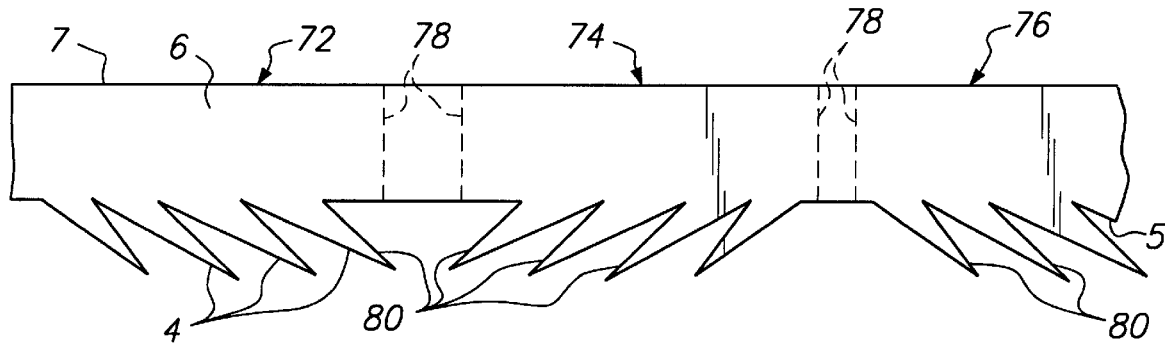
FIG. 6 is a front elevational view of a portion of a fourth embodiment of a sheet member prior to forming the sheet member into a pattern.
Figure 7:
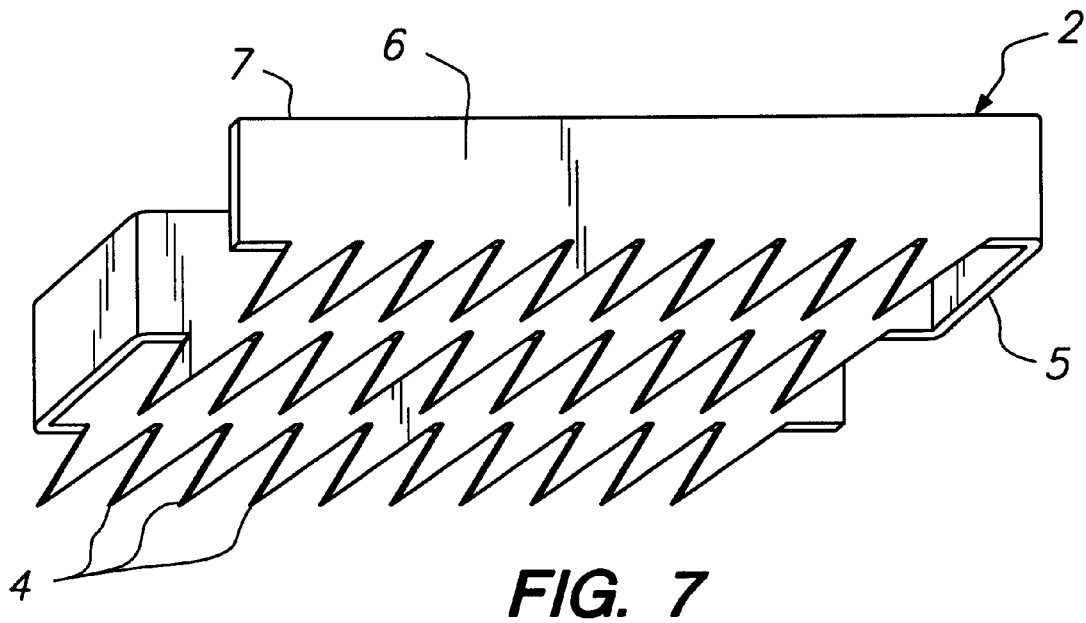
FIG. 7 is a bottom perspective view of the sheet member of FIG. 6 after being formed into a pattern.
Figure 8:
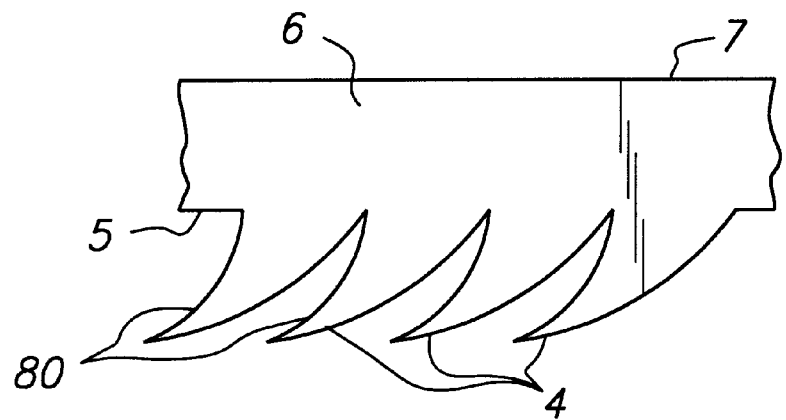
FIG. 8 is an alternate embodiment for microprotrusions on the sheet member.
Figure 9:
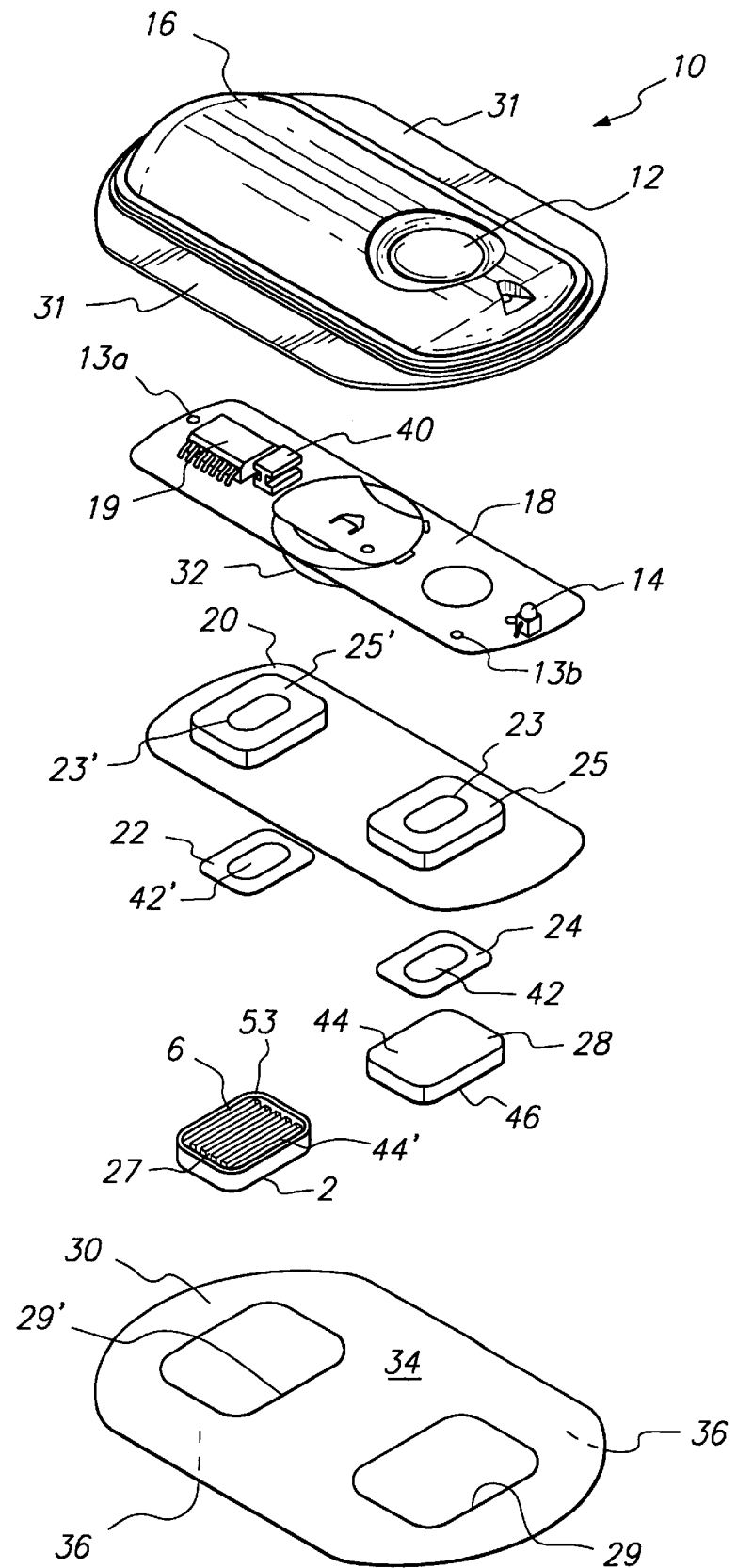
FIG. 9 is an exploded perspective view of one embodiment of an electrotransport agent delivery/sampling system according to one embodiment of the present invention.
Figure 10:
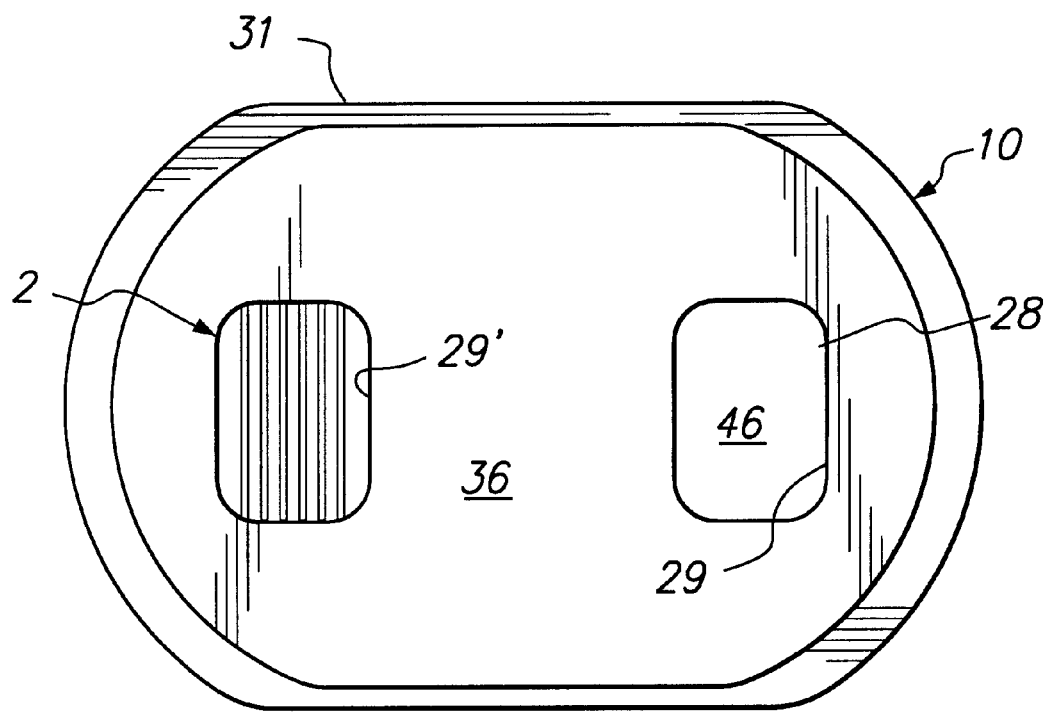
FIG. 10 is a bottom plan view of the electrotransport agent delivery/sampling system of FIG. 9.
Figure 11:
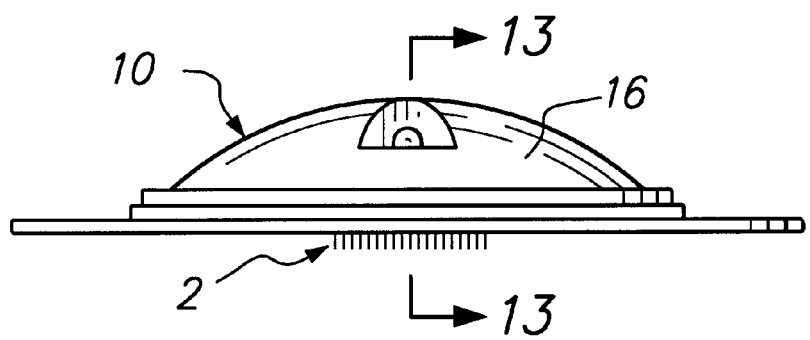
FIG. 11 is a right side elevational view of the electrotransport agent delivery/sampling system of FIG. 9.
Figure 12:
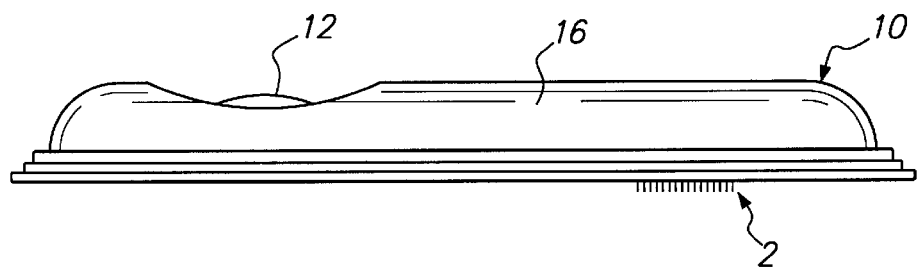
FIG. 12 is a rear elevational view of the electrotransport agent delivery/sampling system of FIG. 9.
Figure 13:
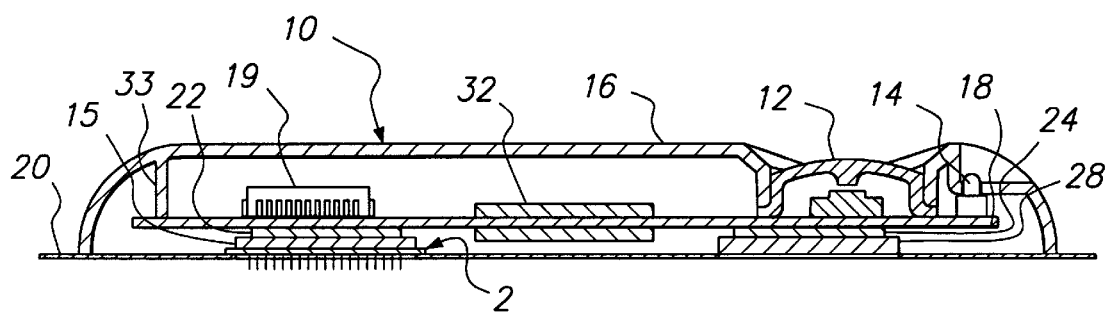
FIG. 13 is a cross-sectional view taken along line 13—13 of the assembled electrotransport agent delivery/sampling system of FIG. 11.

The microprotrusion configurations of FIGS. 6, 7 and 8 facilitate penetration of the body surface but also assist in anchoring the device to the body surface. Sheet member 6 in FIG. 6 has angled or slanted microprotrusions 4. In sections 72 and 76 of sheet member 6, the microprotrusions 4 are slanted to the right along the length of the sheet member 6. In section 74, the microprotrusions are slanted to the left along the length of the sheet member 6. As a result, when sheet member 6 is folded along lines 78 into the serpentine pattern shown in FIG. 7, all of the microprotrusions 4 are slanted in the same direction. With this configuration, the sheet member 6 and elements attached thereto can be slid along the body surface in the direction of the slanted microprotrusions while pressing down on the device to facilitate better penetration against the viscoelastic nature of the body surface. This configuration also aids in anchoring the device to the body surface because the top edges 80 of each of the microprotrusions act similar to the barbs described previously.

Similarly, sheet member 6 in FIG. 8 has curved, sweeping microprotrusions 4. The microprotrusions 4 sweep to the left along the length of the sheet member 6. As a result, when sheet member 6 is formed into a curved configuration, such as for example those of either FIGS. 1 or 3, sheet member 6 and elements attached thereto can be turned clockwise in the direction of the sweeping microprotrusions while pressing down on the device to facilitate better penetration against the viscoelastic nature of the body surface. This configuration also aids in anchoring the device to the body surface because the top edges 80 on each of the microprotrusions act similar to the barbs described previously.

The pattern for the microprotrusion array members 6 can be produced with a photolithography process followed by a chemical etching process. A thin sheet member 6 of metal such as stainless steel or titanium is patterned photolithographically with patterns containing blade-like structures. In general, a thin laminate dry resist or wet resist is applied on the sheet member 6 which typically has a thickness of about 7 $\mu$m to about 100 $\mu$m, preferably about 25 $\mu$m to about 50 $\mu$m. The resist is contact exposed using a mask having the desired pattern and is subsequently developed. These operations are conducted in much the same way that they are for the manufacture of a printed circuit board. The sheet member 6 is then etched using acidic solutions. After the pattern has been etched, the sheet member 6 is rolled or folded into the desired configuration (i.e., spiral, serpentine, concentric circles, etc.) having voids 27 for holding the agent-containing reservoir. The finished structure provides microprotrusions 4 at the skin proximal edge 5 of sheet member 6. The adjacent turns of member 6 (see FIGS. 1 and 5) form adjacent vertical walls between which are voids 27 containing a reservoir 8 (e.g., a gel reservoir; see FIG. 5) for containing an agent (e.g., a drug) therein or for the passage of an agent therethrough when the sheet member 6 is applied to the body surface.

In one embodiment of the etching process, a dry resist (e.g., "DYNACHEM FL" (available from Dynachem located in Tustin, Calif.) is applied 12.5 $\mu$m thick to one or both sides of the sheet member 6 and exposed in a standard manner. Then using a suitable spray etcher (e.g., "DYNAMIL VRP 10/NM" available from Western Tech. Assoc. located in Anaheim, Calif.) a mixture of ferric chloride, water and hydrochloric acid is sprayed onto the resist and sheet member 6 at about 52° C. for two minutes. A standard caustic stripper is used for the resist removal.

In another embodiment of the etching process, a wet resist (e.g., "SHIPLEY 111S" available from Shipley Corporation, located in Marlborough, Mass.) is applied 7.5 $\mu$m thick at about 21° C. to one or both sides of the sheet member 6 and exposed in a standard manner. Then a suitable etchant (e.g., ferric chloride) is sprayed onto the resist and sheet member at about 49° C. A standard caustic stripper is used for the resist removal.

The sheet member 6 and microprotrusions 4 are made from materials that have sufficient strength and manufacturability to produce microprotrusions, such as, glasses, ceramics, rigid polymers, reinforced (e.g., carbon fiber reinforced) polymers, metals and metal alloys. Examples of metals and metal alloys include but are not limited to stainless steel, iron, steel, tin, zinc, copper, gold, platinum, aluminum, germanium, zirconium, titanium and titanium alloys. Each of the sheet member and microprotrusions can have a thin layer of gold, platinum, iridium, titanium, or rhodium plating. Examples of glasses include silicas and devitrified glasses such as "PHOTOCERAM" available from Corning in Corning, N.Y. Examples of polymers include but are not limited to polystyrene, polymethylmethacrylate, polypropylene, polyethylene, "BAKELITE", cellulose acetate, ethylcellulose, styrene/acrylonitrile copolymers, stryrene/butadiene copolymers, acrylonitrile/butadiene/styrene (ABS) copolymers, polyvinyl chloride and acrylic acid polymers including polyacrylates and polymethacrylates.

The number of microprotrusions 4 and reservoirs 8 of any of the embodiments of the sheet member 6 is variable with respect to the desired flux rate, agent being sampled or delivered, delivery or sampling device used (i.e., electrotransport, passive, osmotic, pressure driven, etc.), and other factors as will be evident to one of ordinary skill in the art. In general, the larger the number of microprotrusions per unit area (i.e., microblade density), the less concentrated the flux of the agent in the skin because there are a greater number of pathways through the skin. Consequently with elecrotransport delivery or sampling, a smaller number of microprotrusions per unit area, leads to the transport of the agent through the skin becoming more concentrated in fewer pathways. Higher concentrations of agents in a skin pathway can lead to higher incidences and/or severity of skin reactions (e.g., irritation). Therefore, larger microblade densities are generally preferred to reduce the incidence and/or severity of skin reactions.

The present invention can also be used for sampling a body analyte (e.g., glucose) transdermally. The analyte to be sampled is extracted through the openings cut in the *stratum corneum* by the microprotrusions 4 and collected in the sampling reservoir 8 (FIG. 5). Known analyte (e.g., glucose) sensing elements can be placed directly in reservoir 8. Alternatively, the reservoir 8 can be removed from the device and suitably processed in order to determine the amount of analyte collected. Such devices are useful in monitoring the patient's blood glucose concentration (i.e., through appropriate software which correlates the amount of glucose extracted with the concentration of glucose in the blood) and can further be used to adjust a treatment regime which typically includes administration of insulin to the patient and/or appropriate modification of diet and/or exercise.

One embodiment of the present invention relies on the application of an electric current across the body surface or "electrotransport". It will be appreciated by those working in the field that the present invention can be used in conjunction with a wide variety of electrotransport systems, as the invention is not limited in any way in this regard. For examples of electrotransport systems, reference may be had to U.S. Pat. Nos. 5,147,296 to Theeuwes et al., 5,080,646 to Theeuwes et al., 5,169,382 to Theeuwes et al., 5,423,739 to Phipps et al., 5,385,543 to Haak et al., 5,310,404 to Gyory et al., and 5,169,383 to Gyory et al., of which any of the disclosed electrotransport systems can be used with the present invention.

Device 2 and support member 15 when used in an electrotransport system are preferably electrically insulated from an electrode or other electric current conducting members in order to avoid short circuiting the agent-containing, or agent-receiving, reservoir contained in the voids 27, 127. This can be accomplished by using electrically insulative materials or coatings for sheet member 6, 106 and/or support member 15.

FIGS. 9–13 illustrate a representative electrotransport delivery/sampling device 10 that may be used in conjunction with the present invention. Device 10 comprises an upper housing 16, a circuit board assembly 18, a lower housing 20, donor electrode 22, counter electrode 24, donor reservoir in voids 27, counter reservoir 28 and skin-compatible adhesive 30. Upper housing 16 has lateral wings 31 which assist in holding device 10 on a patient's skin. Printed circuit board assembly 18 comprises an integrated circuit 19 coupled to discrete components 40 and battery 32. Circuit board assembly 18 is attached to housing 16 by posts (one post 33 shown in FIG. 13) extending from the lower (skin proximal) surface of housing 16 and passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 31. Shown (partially) on the underside of circuit board assembly 18 is a button cell battery 32. Other types of batteries may also be employed to power device 10 depending on the need.

The device 10 is generally comprised of battery 32, electronic circuitry 19,40, electrodes 22,24, counter reservoir 28, and device 2 with sheet member 6 and donor reservoir 8 therein, all of which are integrated into a self-contained unit. Electrodes 22, 24, donor reservoir 8 and counter reservoir 28 are retained by lower housing 20. The outputs (not shown in FIG. 18) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of the donor reservoir 8 and counter reservoir 28. The bottom side 46 of reservoir 28 contacts the patient's skin through the opening 29 in adhesive layer 30. The bottom side 46' of the donor reservoir 8 contacts the patient's skin through opening 29'. The agent (e.g., drug) in the donor reservoir 8 is typically in the form of a solution, most preferably an aqueous solution, which solution is contained in a solid matrix material such as a sponge, a hydrophilic polymer matrix (e.g., a hydrogel) which allows free mobility of the agent therethrough. The reservoir matrix material fills the voids 127 between adjacent sheet members 106 (as is more clearly shown in FIG. 15) such that the agent reservoir 8 is in contact with the body surface.

The device 10 adheres to the patient's body surface (e.g., skin) by means of a peripheral adhesive layer 30 (which has upper adhesive side 34 and body-contacting adhesive side 36) and, optionally, anchoring elements on the device 2 of any of the embodiments discussed herein. The adhesive side 36 covers the entire underneath side of the device 10 except where the device 2 and the counter electrode reservoirs are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and agent reservoirs within housing depression 25, 25' as well as retains device 2 to lower housing 20 and lower housing 20 to upper housing 16.

In one embodiment of the agent delivery/sampling device there is a release liner (not shown) on the device 10 for maintaining the integrity of adhesive layer 30 when the device is not in use. In use, the release liner is stripped from the device before the device is applied to the skin. Device 10 also has a push button switch 12, which when pressed turns the device 10 on which is made apparent to the user by means of LED 14 becoming lit. Agent is delivered through the patient's skin (e.g., on the arm) by electrotransport over the predetermined delivery interval.

Figure 14:
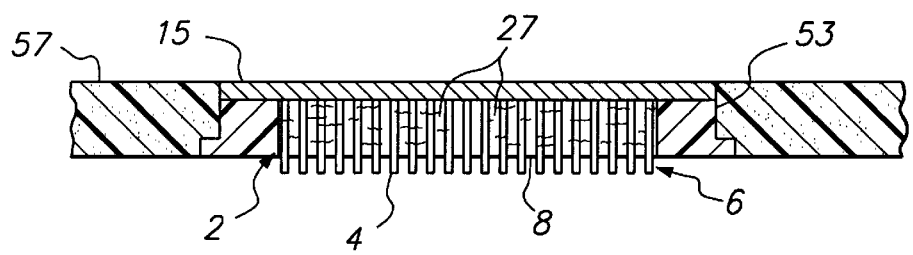
FIG. 14 is a diagrammatic cross-sectional view of a passive agent delivery/sampling system in accordance with one embodiment of the present invention.

In other embodiments of the present invention, passive transdermal delivery or sampling devices are used with the device 2. It will be appreciated by those working in the field that the present invention can be used in conjunction with a wide variety of passive transdermal systems, as the invention is not limited in this regard. For examples of passive systems, reference may be had to, but not limited to, U.S. Pat. Nos. 4,379,454 to Campbell et al., 4,588,580 to Gale et al., 4,832,953 to Campbell et al., 4,698,062 to Gale et al., 4,867,982 to Campbell et al., and 5,268,209 to Hunt et al., of which any of the disclosed systems can be used with the present invention. One example of a passive transdermal delivery/sampling device is illustrated in FIG. 14. Optional support member 15 having the body distal edge of sheet member 6 embedded therein is housed in an outer housing 53 and a foam pad or band 57 which can be applied to the body surface. The edges of sheet member 6 need not be embedded in the support member 15. Support member 15 is sufficiently rigid so as not to deform when force is applied thereto and so as to more evenly transmit the applied force to the top edge of the sheet member 6 across the width and length of device 2. Preferably, although not required, the passive delivery/sampling device has a peripheral adhesive on the body-contacting surface of foam pad 57.

It will be appreciated by those working in the field that the present invention can also be used in conjunction with a wide variety of osmotic and pressure driven agent delivery or agent sampling systems, as the invention is not limited to a particular device in this regard. For examples of osmotic and pressure driven devices, reference may be had to U.S. Pat. Nos. 4,340,480 to Eckenhoff, 4,655,766 to Theeuwes et al., 4,753,651 to Eckenhoff, 5,279,544 to Gross et al., 4,655,766 to Theeuwes, 5,242,406 to Gross et al., and 4,753,651 to Eckenhoff any of which can be used with the present invention.

This invention has utility in connection with the delivery of agents within any of the broad class of drugs normally delivered through body surfaces and membranes, including skin. In general, this includes drugs in all of the major therapeutic areas. The invention is also useful in the transdermal delivery of proteins, peptides and fragments thereof, whether naturally occurring, chemically synthesized or recombinantly produced. The invention may additionally be used in conjunction with the delivery of vaccines, nucleotidic drugs, including oligonucleotide drugs, polynucleotide drugs, and genes. These substances typically have a molecular weight of at least about 300 daltons, and more typically have a molecular weight of at least about 300 to 40,000 daltons. As mentioned, the device 2 of the present invention can also be used with sampling devices including, but not limited to, reverse electrotransport (i.e., reverse iontophoresis and/or reverse electroosmosis in the case of sampling uncharged materials such as glucose), osmosis, and passive diffusion. For example, reference may be had to U.S. Pat. Nos. 4,756,314 to Eckenhoff et al., 5,438,984 to Schoendorfer, 5,279,543 to Glikfeld et al., and 5,362,307 to Guy et al.

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A device for use in introducing or withdrawing an agent through a body surface, comprising:
    a sheet member having a plurality of microprotrusions extending from an edge of the sheet member and in a direction defined by a plane of the sheet member, for piercing the body surface, the sheet member having a configuration which defines a void, the sheet member when in use being oriented in an approximately perpendicular relation to the body surface with the edge having the microprotrusions being proximal the body surface;
    an agent-containing or agent-receiving reservoir in the void, the reservoir when in use being in agent transmitting communication with the body surface and
    means for holding the sheet member on the body surface; the means for holding being selected from the group consisting of anchoring barbs on the microprotusions, angled microprotrusions, curved microprotrusions, an adhesive, a tape, a strap and a bandage.

2. The device of claim 1, wherein a plurality of said sheet members are fastened together.

3. The device of claim 2, wherein said sheet members are fastened together in spaced and roughly parallel orientation.

4. The device of claim 1, wherein the sheet member has a spiral configuration and the void is defined by adjacent spirals.

5. The device of claim 1, wherein the sheet member has a serpentine configuration and the void is defined by adjacent folds.

6. The device of claim 1, wherein the sheet member comprises a plurality of concentric circles and the void is defined by adjacent concentric circles.

7. The device of claim 1, wherein the reservoir is an agent-containing reservoir.

8. The device of claim 7, wherein the agent is a therapeutic agent.

9. The device of claim 8, wherein the agent is a therapeutic drug.

10. The device of claim 7, further comprising a therapeutic agent delivery device.

11. The device of claim 10, wherein the delivery device comprises a transdermal drug delivery device.

12. The device of claim 1, wherein the reservoir is an agent-receiving reservoir.

13. The device of claim 12, wherein the agent is a body analyte.

14. The device of claim 13, wherein the body analyte is glucose.

15. The device of claim 12, further comprising an agent sampling device.

16. The device of claim 15, wherein the sampling device samples glucose and measures or estimates concentrate of glucose in the body.

17. The device of claim 1, further comprising a rigid structural support extending across at least a portion of the sheet member configuration.

18. The device of claim 17, wherein the rigid structural support contacts a second edge of the sheet member which second edge is opposite the edge having the microprotrusions.

19. The device of claim 1, wherein the means for holding comprises an adhesive.

20. A device for use in introducing or withdrawing an agent through a body surface, comprising:
    a sheet member having a plurality of microprotrusions for piercing the body surface, the microprotrusions extending from a body surface proximal edge of the sheet member and in a direction defined by a plane of the sheet member, the sheet member having a configuration which defines a void;
    an agent-containing or agent-receiving reservoir in the void, the reservoir when in use being in agent transmitting communication with the body surface;
    a support which contacts and extends across a second edge of the sheet member; and
    means for holding the sheet member on the body surface, the means for holding being selected from the group consisting of anchoring barbs on the microprotrusions, angled microprotrusions, curved microprotrusions, an adhesive, a ea strap and a bandage.

21. The device of claim 20, wherein a plurality of said sheet members are fastened together.

22. The device of claim 21, wherein said sheet members are fastened together in spaced and roughly parallel orientation.

23. The device of claim 20, wherein the sheet member comprises a spiraled sheet.

24. The device of claim 20, wherein the sheet member comprises a serpentine-shaped sheet.

25. The device of claim 20, wherein the sheet member comprises a first cylindrical sheet and the device further comprises a second cylindrical sheet having a diameter less than a diameter of the first cylindrical sheet.

26. The device of claim 20, wherein the means for holding comprises an adhesive.

* * * * *

UNITED STATES PATENT AND TRADEMARK OFFICE
CERTIFICATE OF CORRECTION

PATENT NO. : 6,050,988
DATED : April 18, 2000
INVENTOR(S) : Michael G. Zuck

It is certified that error appears in the above-identified patent and that said Letters Patent is hereby corrected as shown below:

Column 12, line 45, "ea" should read --tape, a--.

Signed and Sealed this

Twenty-seventh Day of March, 2001

Attest:

NICHOLAS P. GODICI

Attesting Officer

Acting Director of the United States Patent and Trademark Office